(12) United States Patent
Terrell et al.

(10) Patent No.: US 8,058,482 B2
(45) Date of Patent: Nov. 15, 2011

(54) METHOD FOR THE PREPARATION OF SEVOFLURANE

(75) Inventors: Ross C. Terrell, New Port Richey, FL (US); Joshua A. Levinson, Zionsville, PA (US); Charles W. Young, Nazareth, PA (US)

(73) Assignee: Piramal Critical Care, Inc., Orchard Park, NY (US)

( * ) Notice: Subject to any disclaimer, the term of this patent is extended or adjusted under 35 U.S.C. 154(b) by 0 days.

(21) Appl. No.: 11/281,293

(22) Filed: Nov. 17, 2005

(65) Prior Publication Data

US 2006/0205825 A1    Sep. 14, 2006

Related U.S. Application Data

(60) Provisional application No. 60/628,707, filed on Nov. 17, 2004.

(51) Int. Cl.
*C07C 43/13* (2006.01)
(52) U.S. Cl. .......................... 568/682; 568/683
(58) Field of Classification Search .................. None
See application file for complete search history.

(56) References Cited

U.S. PATENT DOCUMENTS

| 4,874,901 | A | 10/1989 | Halpern et al. | |
|---|---|---|---|---|
| 6,100,434 | A | 8/2000 | Bieniarz et al. | |
| 6,362,273 | B1 | 3/2002 | Martin et al. | |
| 2003/0158435 | A1* | 8/2003 | Joyce et al. | 560/24 |

FOREIGN PATENT DOCUMENTS

| EP | 0 129863 | 2/1985 |
|---|---|---|
| GB | 2219292 | 12/1989 |
| WO | WO 9821219 A1 * | 5/1998 |

OTHER PUBLICATIONS

Bieniarz et al., An efficient and environmentally friendly synthesis of the inhalation anesthetic sevoflurane, Journal of Fluorine Chemistry, vol. 106, Jun. 2000, pp. 99-102.*

Halpern et al., Top 10 Opportunities to Improve Process Performance and Profit Using Phase Transfer Catalysis, Industrial Phase Transfer Catalysis, Issue 16, 2002, pp. 1-16.*

Ramakrishna et al., "A Safe and Efficient Process for the Synthesis of the Inhalation Anesthetic Sevoflurane" Organic Process Research & Development, 2000, 4, 581-584.

Halpern, et al., "Replacement of Halogens by Fluorine" Chemistry of Organic Fluorine Compounds II, In: Hudlicky and Pavlath, Chemistry of Organic Fluorine Compounds II a Critical Review, ACS Monograph 187, American Chemical Society, Washington, DC, 1995, 172-198.

* cited by examiner

*Primary Examiner* — Rosalynd Keys
(74) *Attorney, Agent, or Firm* — Reed Smith LLP; Nanda P.B.A. Kumar; Matthew P. Frederick

(57) ABSTRACT

A method for the preparation of $(CF_3)_2CHOCH_2F$ (Sevoflurane) is presented, which comprises providing a mixture of $(CF_3)_2CHOCH_2Cl$, potassium fluoride, water, and a phase transfer catalyst and reacting the mixture to form $(CF_3)_2CHOCH_2F$.

21 Claims, No Drawings

METHOD FOR THE PREPARATION OF SEVOFLURANE

CROSS REFERENCE TO RELATED APPLICATIONS

Applicants claim priority based on U.S. provisional patent application No. 60/628,707, filed on Nov. 17, 2004 and entitled "Method for the Preparation of Sevoflurane," the disclosure of which is hereby incorporated by reference.

FIELD OF THE INVENTION

The present invention relates to the field of inhalation anesthetics. In particular, the present invention relates to a method for the preparation of $(CF_3)_2CHOCH_2F$ (i.e., Sevoflurane).

BACKGROUND OF THE INVENTION

This invention relates to a process for fluorinating $(CF_3)_2CHOCH_2Cl$ to produce $(CF_3)_2CHOCH_2F$ (Sevoflurane), which is a valuable inhalation anesthetic, especially useful in outpatient procedures and for conscious sedation.

There are many methods that can be used to synthesize fluorinated compounds such as Sevoflurane. One of the most useful is to first prepare the chloro-substituted compound, $(CF_3)_2CHOCH_2Cl$ (sevochlorane), the preparation of which is described in U.S. Pat. Nos. 3,476,860 and 3,683,092, followed by fluorination via a halogen exchange reaction. See Equation (1).

$$(CF_3)_2CHOCH_3 \rightarrow (CF_3)_2CHOCH_2Cl \rightarrow (CF_3)_2CHOCH_2F \quad (1)$$

However, it has been found that the use of potassium fluoride in the halogen exchange reaction can be hampered by a low yield of fluorinated products, caused by, among other things, side reactions that produce elimination and hydrolysis products. In particular, when water is present in appreciable quantities, it has been found that hydrolysis products can be formed in large amounts, creating impurities that must be removed as well as severely reducing the yield of the desired fluorinated product.

For example, the reaction of chloroalkanes with potassium fluoride has been reported using a variety of methods. Landini, et al. (Synthesis, 1428 (1974)) reported the reaction of alkyl halides with potassium fluoride in the presence of phase transfer catalysts to yield alkyl fluorides. The reactions were not done with anhydrous potassium fluoride but were done in an aqueous medium. In this medium, there was significant hydrolysis to give alcohol by-products.

The effect of water on the reaction of potassium fluoride with halo-alkanes in the presence of phase transfer catalysts has been described by Dermeik, et al. (J. Org. Chem., Vol. 50, pp. 879-882, 1985). The reference indicates that low water content with respect to the fluorinating agent corresponds to low production of hydrolysis products. The data indicate that the potassium fluoride to water molar ratio must be greater than 15 in order for the hydrolysis products to fall to less than 4 mol % in the final product mixture.

Escoula, et al. (Tetrahedron Letters, Vol. 27, No. 13, pp. 1499-1500 (1985)) state that formamide is superior to water as a reaction medium for a fluoride-chloride exchange reaction employing phase transfer catalysts. Higher yields are obtained under these conditions.

Thus, if yield is important, the fluorination reaction has generally been performed in conditions under which the solvent is, at least predominantly, something other than water.

For example, U.S. Pat. No. 3,683,092, mentioned above, describes the fluorination of $(CF_3)_2CHOCH_2Cl$ with potassium fluoride, using sulfolane (tetrahydrothiophene-1,1 dioxide) as a solvent; see Equation (2).

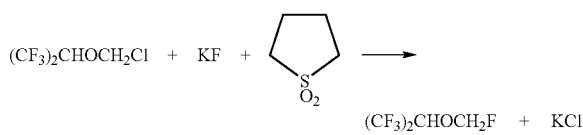

The references above generally concern the fluorination of chloroalkanes. One of skill in the art will recognize that in the case of chloroethers, the issue of hydrolysis in the presence of water to give ether cleavage is expected to be even more of a concern. In particular, 2-chloro-ethers are well known to be more easily hydrolyzed than alkanes in the presence of water. In other literature concerning the fluorination of chloroethers, the presence of water during fluorination of chloroethers is tightly controlled or scrupulously avoided to the point of complete elimination or avoidance.

The use of potassium fluoride as a reagent for the replacement of chlorine in organic compounds has been reviewed in M. Hudlicky, Chemistry of Organic Fluorine Compounds, $2^{nd}$ Revised Edition, Ellis Horwood Ltd. (1992). The reference teaches that potassium fluoride has been successfully applied to the replacement of even poorly reactive halogen atoms, and that the success of this method lies in the application of suitable solvents such as acetamide, nitrobenzene, dimethyl sulfoxide, dimethyl sulfone, tetra methylene sulfone, and especially ethylene glycol and diethylene glycol. The reference also teaches that to obtain maximum yields, pure and absolutely dry (i.e., no water) chemicals must be used. The above is specifically taught with respect to halogen-containing ethers, among other things.

The fluorination of $(CF_3)_2CHOCH_2Cl$ using anhydrous potassium fluoride and without the addition of solvent is described in U.S. Pat. No. 4,874,901. The reaction is carried out at high temperatures (185° C.-283° C.). Reaction pressures as high as 1100 psig are disclosed. Sevoflurane is synthesized using this method, resulting in a 60% conversion and a 75% yield.

U.S. Pat. No. 6,100,434 also describes the effect of water on the fluorination of $(CF_3)_2CHOCH_2Cl$. It discloses that, while the presence of water can be tolerated, high levels of water increase the likelihood of hydrolysis. Furthermore, the reference discloses that higher levels of water are likely to impede the fluorination reaction due to the relative immiscibility of the $(CF_3)_2CHOCH_2Cl$ in water. The reference also teaches that water, if used at all in the reaction, is used as a co-solvent (i.e., it is not used without the presence of another solvent material).

However, water is a convenient solvent to use. It is also often present in reactants and fluorinating agents that are commonly used in fluorination reactions, and in such cases, its presence during the fluorination reaction is difficult to avoid without extra purification steps. However, water is not as difficult to remove from reaction products as many other types of impurities. Thus, a high yield, low hydrolysis fluorination reaction of chloroethers, such as $(CF_3)_2CHOCH_2Cl$, in an aqueous medium would be welcomed in the art.

SUMMARY OF THE INVENTION

Surprisingly, it has been discovered that $(CF_3)_2CHOCH_2Cl$ can be reacted with potassium fluoride in the presence of a water and a phase transfer catalyst, preferably without the presence of an organic co-solvent, to give good conversions and yields of $(CF_3)_2CHOCH_2F$ (Sevoflurane), with only minimal hydrolysis. For example, in fluorinations conducted according to the method of the present invention, it is not unusual for less than 5 wt % of the sevochlorane charged to the reaction vessel to undergo hydrolysis, and for the molecular yield to be greater than 50% based upon the amount of sevochlorane consumed in the reaction.

Thus, the present invention provides a novel process for the preparation of $(CF_3)_2CHOCH_2F$. The process comprises reacting $(CF_3)_2CHOCH_2Cl$ with potassium fluoride in the presence of water and a phase transfer catalyst. The reaction can be done at moderate temperatures and pressures and with minimal hydrolysis of $(CF_3)_2CHOCH_2Cl$ to $(CF_3)_2CHOH$.

DETAILED DESCRIPTION OF THE INVENTION

In the process of the present invention, the starting compound $(CF_3)_2CHOCH_2Cl$ is reacted with potassium fluoride in the presence of water and a phase transfer catalyst. The starting compound $(CF_3)_2CHOCH_2Cl$ is a well known compound and can be prepared using a number of synthetic routes. For example, its synthesis is described in U.S. Pat. Nos. 3,476,860 and 3,683,092. While $(CF_3)_2CHOCH_2Cl$ is typically introduced into the fluorination reaction in a purified form, purification is not generally essential to realize the benefits of the invention. Thus, if desired, the fluorination reaction can be conducted in the same vessel or space as the preparation of the starting material $(CF_3)_2CHOCH_2Cl$, making possible a "one-pot synthesis" of sevoflurane.

The fluorination reaction can be conducted in many ways. Typically, it is carried out in a batch mode by mixing $(CF_3)_2CHOCH_2Cl$, potassium fluoride, water, and a phase transfer catalyst to form a reaction mixture, and subsequently heating the reaction mixture with stirring or another form of agitation for a period of time. The order of addition of the four components is not critical. The reaction can be carried out in a semi-batch mode, where one or more reactants or products are added or removed continuously as the reaction mixture is heated and agitated. For example, if adding material to a semi-batch process, the added reactant (or "limiting" reactant) can be the sevochlorane (which is added to the water/potassium fluoride/phase transfer catalyst solution) or the water/potassium fluoride solution (which is added to the sevochlorane/catalyst mixture). A continuous mode of operation is also possible, where the reactants and catalyst are added continuously to form a reaction mixture that is heated and agitated with a continuous removal of sevoflurane product.

The reaction is preferably done in the temperature range of 60° C. to 100° C., although temperatures outside this range can be used, with higher temperatures generally corresponding to a higher fluorination rate. The pressure of the reaction can be as low as 0 psig and is preferably in the range of 0 to 105 psig. Reaction pressure is typically a function of the temperature of the reaction and its mode of operation (i.e., closed vs. vented vessel). Generally, higher pressures correspond to higher temperatures and to those modes of reaction that see an accumulation of gaseous reaction products.

Typical reaction times are in the range of from about three hours to sixteen hours, however, reaction time can depend upon how the reaction is conducted, and the reaction time can be outside this range. For instance, the reaction rate of a continuous or semibatch reaction can be kinetically limited by the addition or removal of a reactant (such as potassium fluoride or $(CF_3)_2CHOCH_2Cl$). Furthermore, reaction time will also depend upon temperature, with higher temperatures tending to correspond with higher rates of fluorination and shorter reaction times.

The potassium fluoride to be used can be commercially obtained in various forms, including flakes, granules (coarse or fine), or as an aqueous solution. It need not be anhydrous, dried, or finely divided. The potassium fluoride can also be used as a hydrate salt (e.g., the dihydrate, $KF-2H_2O$, and the tetrahydrate, $KF-4H_2O$), which can be provided in granular, flake, or other forms. In addition, part or all of the potassium fluoride can be introduced as the acid salt (i.e., $KHF_2$), which may also be obtained in flake, granular, or aqueous solution form; use of the acid salt to provide a portion of the available fluoride ion generally appears to increase the yield of the fluorinated product with respect to the use of potassium fluoride alone. The molar amount of potassium fluoride to be used per mole of $(CF_3)_2CHOCH_2Cl$ is typically above 0.1:1 and is preferably in the range of 1:1 to 2:1; however, this invention is not limited to these preferred quantities.

The weight of combined fluoride salts (i.e., potassium fluoride and potassium bifluoride) should be above 25 wt % relative to the combined weight of the fluoride salts and water used in the reaction, with a preferred range of about 35 wt % to about 50 wt %. However, this invention is not limited to these preferred quantities, as significant amounts of sevoflurane can be produced with relative weights above or below this range; variations in conversion, yield, and hydrolysis are affected by the actual weight used in the reaction.

If desired, one or more aqueous acids can be used in the reaction (in addition to the $(CF_3)_2CHOCH_2Cl$, phase transfer catalyst, KF, and water) to promote the formation of $(CF_3)_2CHOCH_2F$. Suitable acids include hydrochloric acid or hydrofluoric acid; other organic and inorganic acids may be also used. The acids are preferably present in amounts which are in the range of 1 to 3 wt % based upon the weight of the $(CF_3)_2CHOCH_2Cl$ charged to the reaction; however, this invention is not limited to these preferred quantities, as smaller or larger amounts of acid will generally still give the low hydrolysis benefits of the present invention.

The quantity of water to be used is typically above 1 wt % based upon the weight of the $(CF_3)_2CHOCH_2Cl$ charged to the reaction and is preferably in the range of 10 to 50 wt %. However, this invention is not limited to these preferred quantities, as more or less water may be used to achieve appreciable formation of fluorinated product. While it is most preferred that the water added to the reaction mixture be essentially free of other solvents or impurities (i.e., at levels less than 1 wt % of the water added), these materials may be present in amounts preferably not greater than 50 wt % and more preferably not greater than 20 wt %. Examples include dissolved salts, water-soluble organic compounds, organic solvents, etc., which may be present as unavoidable impurities or as functional components.

Sevoflurane is generally produced at molecular yields above 50%, and more preferably above 60%, based upon the molar amount of the sevochlorane reacted. Hydrolysis products $((CF_3)_2CHOH)$ are generally below 15 wt %, and preferably below 10 wt %, based upon the weight of the sevochlorane charged to the reaction.

A wide range of phase transfer catalysts can be used. Commercially available phase transfer agents include quaternary ammonium salts (such as Aliquat 175, Aliquat 336, and benzyl triethyl ammonium chloride), quaternary phosphonium salts (such as butyl triphenyl phosphonium chloride and methyl triphenyl phosphonium bromide), polyglycols (such as polyethylene glycol dibutyl ethers and polyethylene glycol dimethyl ethers), crown ethers (such as 18-crown-6 and dibenzo-18-crown-6), ionic liquids (such as guanidiniums and imidazoliums), chiral compounds (such as anthracenyl-methyl cinchonidinium chloride), and high-temperature agents (such as Aliquat HTA-1). However, this invention is not limited to these specific compounds, and other phase transfer catalysts from the above categories and their combinations can be used. The amount of phase transfer catalyst to be used is generally present in amounts above 0.25 wt % based upon the weight of the $(CF_3)_2CHOCH_2Cl$ charged to the reaction and is typically in the range of 1 to 5 wt %; however, this invention is not limited to these preferred quantities, as a greater or smaller proportion of phase transfer agent may be used to provide appreciable formation of the fluorinated product without appreciable hydrolysis.

The reaction product $(CF_3)_2CHOCH_2F$ (Sevoflurane) can be isolated by washing the reaction mixture with water or by azeotropic distillation with or without additional water. This crude reaction product can be further purified by fractional distillation. Other purification and separation methods known in the art can be used to recover or further purify the Sevoflurane product, which may include methods that utilize vapor phase chromatography, extraction, absorption, and stripping.

The following examples will serve to more fully illustrate the practice of preferred embodiments of the present invention. Such examples are intended to be for illustrative purposes only and are not intended to limit the scope of the invention. In these examples, the following commercially available phase transfer catalysts (Cognis Corporation, 2505 South Kensington Road, Kankakee, Ill. 60901) were used and are identified as follows:

| | |
|---|---|
| Aliquat 175 | Methyl tetrabutyl ammonium chloride |
| Aliquat 100 | Tetrabutylammonium bromide |
| Aliquat 336 | Tricapryl methylammonium chloride |
| Aliquat HTA-1 | Proprietary blend of alkyl ammonium chlorides |

Gas chromatographic analyses were done using an SE-30 column programmed at 55° C. for four minutes then raised to 130° C. at 4° per minute. All weight percents in the examples below are based upon the total weight of the recovered product mixture. The weight of "recovered product mixture" does not include the weights of hydrochloric acid and formaldehyde reaction products which are generally lost in post-reaction processing and/or purification steps. Conversion is calculated as the moles of $(CF_3)_2CHOCH_2Cl$ reacted divided by the moles of $(CF_3)_2CHOCH_2Cl$ charged to the reaction vessel, and yield is calculated as the moles of $(CF_3)_2CHOCH_2F$ formed divided by the moles of $(CF_3)_2CHOCH_2Cl$ reacted.

EXAMPLE 1

Reaction of Chloroether Starting Material with Water

A mixture of 15 g (0.069 mol) of $(CF_3)_2CHOCH_2Cl$ and 15 g of water was heated with stirring in a 100 cc autoclave for 1.5 hours at 90° C. The product was recovered by azeotropic distillation using a Dean Stark trap. The recovered product weighed 13.4 g and was analyzed by gas chromatography. The product was 78.6% $(CF_3)_2CHOCH_2Cl$ and 21.2% $(CF_3)_2CHOH$, indicating significant hydrolysis. Conversion was 30%.

EXAMPLE 2

Fluorination of Chloroether Without Use of Additional Water

A slurry of 43.2 g (0.2 mol) of $(CF_3)_2CHOCH_2Cl$, 11.6 g (0.2 mol) of potassium fluoride, 1.56 g (0.02 mol) potassium bifluoride, and 1 g of Aliquat HTA-1 was heated with stirring in a 100 cc autoclave for 3 hours at 100° C.; no additional water was added, with the only water coming from the HTA-1 solution (less than 0.6 g). The product was isolated by azeotropic distillation from water using a Dean Stark trap. The recovered product weighed 30.1 g and was analyzed using gas chromatography. The product was 75% $(CF_3)_2CHOCH_2F$, 19% $(CF_3)_2CHOCH_2Cl$, and 3% $(CF_3)_2CHOH$. Conversion was 87% and yield was 65%. Yield was considerably lower than conditions using additional water. This example demonstrates a lower yield being obtained when a fluorination is performed using an amount of water which is lower than 10 wt % based upon the weight of the $(CF_3)_2CHOCH_2Cl$ charged to the reaction vessel while using the appropriate amount of catalyst and potassium fluoride salts.

EXAMPLE 3

Fluorination of Chloroether Without Use of Phase Transfer Catalyst

A mixture of $(CF_3)_2CHOCH_2Cl$ 43.2 g (0.2 mol), 40% aqueous potassium fluoride solution 29 g (0.2 mol KF content), and potassium bifluoride 1.56 g (0.02 mol) dissolved in 2.34 g water was heated with stirring in a 100 cc autoclave for 12 hours at 90° C.; no phase transfer catalyst was used. The product was recovered by azeotropic distillation using a Dean Stark trap. The recovered product weighed 38.3 g and was analyzed by gas chromatography. The product was 34.9% $(CF_3)_2CHOCH_2F$, 60.1% $(CF_3)_2CHOCH_2Cl$, and 4.7% $(CF_3)_2CHOH$. Conversion was 47% and yield was 71.7%. Low conversion and yield were observed, which indicates that the phase transfer catalyst is necessary for higher conversion and yield in the presence of water.

EXAMPLE 4

Fluorination of Chloroether with Significant Excess of Water

A mixture of $(CF_3)_2CHOCH_2Cl$ 21.6 g (0.1 mol), potassium fluoride 5.8 g (0.1 mol), potassium bifluoride 0.78 g (0.01 mol), 59.98 g of water, and 0.5 g of Aliquat HTA-1 was heated with stirring in a 100 cc autoclave for 12 hours at 90° C. The product was recovered by azeotropic distillation using a Dean Stark trap. The recovered product weighed 17.0 g and was analyzed by gas chromatography. The product was 22.8% $(CF_3)_2CHOCH_2F$, 0.75% $(CF_3)_2CHOCH_2Cl$, and 74.4% $(CF_3)_2CHOH$. Conversion was 99.4% and yield was 19.5%. This example demonstrates that both low yield of sevoflurane and significant hydrolysis are observed when water is present in amounts above about 50 wt % (based upon the weight of the $(CF_3)_2CHOCH_2Cl$ charged to the reaction vessel) while using the appropriate amount of catalyst and potassium fluoride salts.

EXAMPLE 5

Fluorination as a Function of $KF/KHF_2$ Concentration in Excess Water

A series of experiments were performed to study the effect of potassium fluoride salt concentration on the fluorination in the presence of excess water.

1. A mixture of $(CF_3)_2CHOCH_2Cl$ 21.6 g (0.1 mol), potassium fluoride 5.8 g (0.1 mol), potassium bifluoride 0.78 g (0.01 mol), 31.1 g of water, and 0.5 g of Aliquat HTA-1 was heated with stirring in a 100 cc autoclave for 3 hours at 90° C. The product was recovered by azeotropic distillation using a Dean Stark trap. The recovered product weighed 19.4 g and was analyzed by gas chromatography. The product was 30.98% $(CF_3)_2CHOCH_2F$, 41.83% $(CF_3)_2CHOCH_2Cl$, and 26.38% $(CF_3)_2CHOH$. Conversion was 62% and yield was 48%.

2. A mixture of $(CF_3)_2CHOCH_2Cl$ 21.6 g (0.1 mol), potassium fluoride 7.25 g (0.125 mol), potassium bifluoride 0.975 g (0.0125 mol), 31.1 g of water, and 0.5 g of Aliquat HTA-1 was heated with stirring in a 100 cc autoclave for 3 hours at 90° C. The product was recovered by azeotropic distillation using a Dean Stark trap. The recovered product weighed 19.1 g and was analyzed by gas chromatography. The product was 38.39% $(CF_3)_2CHOCH_2F$, 46.62% $(CF_3)_2CHOCH_2Cl$, and 14.49% $(CF_3)_2CHOH$. Conversion was 59% and yield was 63%.

3. A mixture of $(CF_3)_2CHOCH_2Cl$ 21.6 g (0.1 mol), potassium fluoride 8.7 g (0.15 mol), potassium bifluoride 1.17 g (0.015 mol), 31.1 g of water, and 0.5 g of Aliquat HTA-1 was heated with stirring in a 100 cc autoclave for 3 hours at 90° C. The product was recovered by azeotropic distillation using a Dean Stark trap. The recovered product weighed 19.2 g and was analyzed by gas chromatography. The product was 48.3% $(CF_3)_2CHOCH_2F$, 43.2% $(CF_3)_2CHOCH_2Cl$, and 8.4% $(CF_3)_2CHOH$. Conversion was 61.6% and yield was 75%.

4. A mixture of $(CF_3)_2CHOCH_2Cl$ 21.6 g (0.1 mol), potassium fluoride 10.15 g (0.175 mol), potassium bifluoride 1.365 g (0.0175 mol), 31.1 g of water, and 0.5 g of Aliquat HTA-1 was heated with stirring in a 100 cc autoclave for 3 hours at 90° C. The product was recovered by azeotropic distillation using a Dean Stark trap. The recovered product weighed 19.4 g and was analyzed by gas chromatography. The product was 54.1% $(CF_3)_2CHOCH_2F$, 40.3% $(CF_3)_2CHOCH_2Cl$, and 5.5% $(CF_3)_2CHOH$. Conversion was 64% and yield was 82%.

5. A mixture of $(CF_3)_2CHOCH_2Cl$ 21.6 g (0.1 mol), potassium fluoride 11.6 g (0.2 mol), potassium bifluoride 1.56 g (0.02 mol), 31.1 g of water, and 0.5 g of Aliquat HTA-1 was heated with stirring in a 100 cc autoclave for 3 hours at 90° C. The product was recovered by azeotropic distillation using a Dean Stark trap. The recovered product weighed 19.4 g and was analyzed by gas chromatography. The product was 66.3% $(CF_3)_2CHOCH_2F$, 30.7% $(CF_3)_2CHOCH_2Cl$, and 2.87% $(CF_3)_2CHOH$. Conversion was 72.5% and yield was 89%.

These data indicate that the aqueous salt concentration is an important parameter in determining the conversion of the chloroether to Sevoflurane and for minimizing the generation of the $(CF_3)_2CHOH$ by-product. Lower salt concentrations give lower yields and more hydrolysis, and higher concentrations give higher yields and less hydrolysis.

EXAMPLE 6

A mixture of $(CF_3)_2CHOCH_2Cl$ 21.6 g (0.1 mole), potassium fluoride 8.7 g (0.15 mole), 10 g of water, and 1 g of Aliquat HTA-1 was heated with stirring in a 100 cc autoclave for 17 hours at 60° C. Water was added to dissolve the precipitated salts, and the product was recovered by azeotropic distillation using a Dean Stark trap. The recovered product weighed 18.7 g and was analyzed by gas chromatography. The product was 71.4% $(CF_3)_2CHOCH_2F$ and 26% $(CF_3)_2CHOCH_2Cl$ plus a number of small unidentified byproducts. Conversion was 77.5% and yield was 86%.

EXAMPLE 7

A mixture of $(CF_3)_2CHOCH_2Cl$ 21.6 g (0.1 mole), potassium fluoride 8.7 g (0.15 mole), 10 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 17.4 g and was analyzed by gas chromatography. The product was 89% $(CF_3)_2CHOCH_2F$ and 7% $(CF_3)_2CHOCH_2Cl$. There was 0.6% of $(CF_3)_2CHOH$. Conversion was 94% and yield was 82%.

EXAMPLE 8

A mixture of $(CF_3)_2CHOCH_2Cl$ 21.6 g (0.1 mole), potassium fluoride 8.7 g (0.15 mole), 10 g of water, and 1 g of Aliquat HTA-1 was heated with stirring in a 100 cc autoclave for 4 hours at 100° C. Water was added to dissolve the precipitated salts, and the product was recovered by azeotropic distillation using a Dean Stark trap. The recovered product weighed 17.7 g and was analyzed by gas chromatography. The product was 86.8% $(CF_3)_2CHOCH_2F$ and 9.9% $(CF_3)_2CHOCH_2Cl$. There was only 0.03% $(CF_3)_2CHOH$. Conversion was 92% and yield was 84%.

EXAMPLE 9

A mixture of $(CF_3)_2CHOCH_2Cl$ 21.6 g (0.1 mole), potassium fluoride 8.7 g (0.15 mole), 20 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 18.9 g and was analyzed by gas chromatography. The product was 86% $(CF_3)_2CHOCH_2F$ and 10% $(CF_3)_2CHOCH_2Cl$. There was 0.9% of $(CF_3)_2CHOH$. Conversion was 91% and yield was 89%.

EXAMPLE 10

A mixture of $(CF_3)_2CHOCH_2Cl$ 21.6 g (0.1 mole), potassium fluoride 11.6 g (0.2 mole), 20 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 18 g and was analyzed by gas chromatography. The product was 88.7% $(CF_3)_2CHOCH_2F$ and 6.17% $(CF_3)_2CHOCH_2Cl$. There was only 0.2% $(CF_3)_2CHOH$. Conversion was 95% and yield was 84%.

EXAMPLE 11

A mixture of $(CF_3)_2CHOCH_2Cl$ 43.2 g (0.2 mole), potassium fluoride 12.76 g (0.22 mole), 10 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 38.1 g and was analyzed by gas chromatography. The product was 68.9% $(CF_3)_2CHOCH_2F$ and 29% $(CF_3)_2CHOCH_2Cl$. Conversion was 74% and yield was 88%.

EXAMPLE 12

A mixture of $(CF_3)_2CHOCH_2Cl$ 43.2 g (0.2 mole), potassium fluoride 12.76 g (0.22 mole), 10 g of water, and 2 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 37 g and was analyzed by gas chromatography. The product was 77% $(CF_3)_2CHOCH_2F$ and 20% $(CF_3)_2CHOCH_2Cl$. There was 0.18% $(CF_3)_2CHOH$. Conversion was 83% and yield was 86%.

EXAMPLE 13

A mixture of $(CF_3)_2CHOCH_2Cl$ 43.2 g (0.2 mole), potassium fluoride 12.76 g (0.22 mole), 10 cc of 1.0 N HCl (0.01 mole), and 1 g of Aliquat HTA-1 was heated at 100° C. for 3 hours. Water was added to dissolve the precipitated salts, and the product was recovered by azeotropic distillation using a Dean Stark trap. The recovered product weighed 38.7 g and was analyzed by gas chromatography. The product was 80% $(CF_3)_2CHOCH_2F$ and 18.5% $(CF_3)_2CHOCH_2Cl$. There was 1.05% of $(CF_3)_2CHOH$. Conversion was 83% and yield was 93%.

EXAMPLE 14

A mixture of $(CF_3)_2CHOCH_2Cl$ 21.6 g (0.1 mole), potassium fluoride 6.38 g (0.11 mole), 30 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 16.1 g and was analyzed by gas chromatography. The product was 75% $(CF_3)_2CHOCH_2F$ and 14% $(CF_3)_2CHOCH_2Cl$. There was 8.7% of $(CF_3)_2CHOH$. Conversion was 90% and yield was 67%.

EXAMPLE 15

A mixture of $(CF_3)_2CHOCH_2Cl$ 21.6 g (0.1 mole), potassium fluoride 6.38 g (0.11 mole), 30 g of water, and 0.5 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 14.8 g and was analyzed by gas chromatography. The product was 70% $(CF_3)_2CHOCH_2F$ and 12% $(CF_3)_2CHOCH_2Cl$. There was 11.5% of $(CF_3)_2CHOH$. Conversion was 92% and yield was 57%.

EXAMPLE 16

A mixture of $(CF_3)_2CHOCH_2Cl$ 43.2 g (0.2 mole), potassium fluoride 11.6 g (0.2 mole), 10 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 38.4 g and was analyzed by gas chromatography. The product was 66% $(CF_3)_2CHOCH_2F$ and 32% $(CF_3)_2CHOCH_2Cl$. Conversion was 72% and yield was 89%.

EXAMPLE 17

A mixture of $(CF_3)_2CHOCH_2Cl$ 43.2 g (0.2 mole), potassium fluoride 11.6 g (0.2 mole), 10 g of water, and 1 g of Aliquat HTA-1 was heated with stirring in a 100 cc autoclave for 1 hour at 100° C. Water was added to dissolve the precipitated salts, and the product was recovered by azeotropic distillation using a Dean Stark trap. The recovered product weighed 40.3 g and was analyzed by gas chromatography. The product was 55% $(CF_3)_2CHOCH_2F$ and 43% $(CF_3)_2CHOCH_2Cl$. Conversion was 60% and yield was 93%.

EXAMPLE 18

A mixture of $(CF_3)_2CHOCH_2Cl$ 43.2 g (0.2 mole), potassium fluoride 11.6 g (0.2 mole), 1.56 g of $KHF_2$ (0.02 mole), 10 g of water, and 1 g of benzyl triethyl ammonium dichloride was heated with stirring in a 100 cc autoclave for 3 hours at 100° C. Water was added to dissolve the precipitated salts, and the product was recovered by azeotropic distillation using a Dean Stark trap. The recovered product weighed 37.7 g and was analyzed by gas chromatography. The product was 85.5% $(CF_3)_2CHOCH_2F$ and 9.5% $(CF_3)_2CHOCH_2Cl$. There was 4% $(CF_3)_2CHOH$. Conversion was 92% and yield was 88%.

EXAMPLE 19

A mixture of $(CF_3)_2CHOCH_2Cl$ 43.2 g (0.2 mole), potassium fluoride 11.6 g (0.2 mole), 1.56 g of $KHF_2$ (0.02 mole), 10 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 37.6 g and was analyzed by gas chromatography. The product was 83% $(CF_3)_2CHOCH_2F$ and 15% $(CF_3)_2CHOCH_2Cl$. Conversion was 87% and yield was 90%.

EXAMPLE 20

A mixture of $(CF_3)_2CHOCH_2Cl$ 43.2 g (0.2 mole), potassium fluoride 11.6 g (0.2 mole), 1.56 g of $KHF_2$ (0.02 mole), 20 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 39.2 g and was analyzed by gas chromatography. The product was 75.6% $(CF_3)_2CHOCH_2F$ and 23.3% $(CF_3)_2CHOCH_2Cl$. Conversion was 79% and yield was 94%.

EXAMPLE 21

A mixture of $(CF_3)_2CHOCH_2Cl$ 43.2 g (0.2 mole), potassium fluoride 11.6 g (0.2 mole), 1.56 g of $KHF_2$ (0.02 mole), 10 g of water, and 1 g of Aliquat HTA-1 was heated with stirring in a 100 cc autoclave for 5 hours at 100° C. Water was added to dissolve the precipitated salts, and the product was recovered by azeotropic distillation using a Dean Stark trap. The recovered product weighed 38.6 g and was analyzed by gas chromatography. The product was 80% $(CF_3)_2CHOCH_2F$ and 16% $(CF_3)_2CHOCH_2Cl$. There was 2.5% of $(CF_3)_2CHOH$. Conversion was 86% and yield was 90%.

EXAMPLE 22

A mixture of $(CF_3)_2CHOCH_2Cl$ 43.2 g (0.2 mole), potassium fluoride 11.6 g (0.2 mole), 1.56 g of $KHF_2$ (0.02 mole), 10 g of water, and 1 g of Aliquat 175 was heated with stirring in a 100 cc autoclave for 3 hours at 100° C. Water was added to dissolve the precipitated salts, and the product was recovered by azeotropic distillation using a Dean Stark trap. The recovered product weighed 38.3 g and was analyzed by gas chromatography. The product was 84% $(CF_3)_2CHOCH_2F$ and 11% $(CF_3)_2CHOCH_2Cl$. There was 3.8% of $(CF_3)_2CHOH$. Conversion was 90% and yield was 89%.

EXAMPLE 23

A mixture of $(CF_3)_2CHOCH_2Cl$ 43.2 g (0.2 mole), potassium fluoride 11.6 g (0.2 mole), 1.56 g of $KHF_2$ (0.02 mole), 5 g of water, and 1 g of Aliquat HTA-1 was heated with stirring in a 100 cc autoclave for 3 hours at 100° C. Water was added to dissolve the precipitated salts, and the product was recovered by azeotropic distillation using a Dean Stark trap. The recovered product weighed 37.1 g and was analyzed by gas chromatography. The product was 80.6% $(CF_3)_2CHOCH_2F$ and 15.6% $(CF_3)_2CHOCH_2Cl$. There was 2.6% of $(CF_3)_2CHOH$. Conversion was 87% and yield was 87%.

EXAMPLE 24

A mixture of $(CF_3)_2CHOCH_2Cl$ 21.6 g (0.1 mole), potassium fluoride 17.4 g (0.3 mole), 40 g of water, and 1 g of Aliquat 336 was heated with stirring in a 100 cc autoclave for 16 hours at 60° C. Water was added to dissolve the precipitated salts, and the product was recovered by azeotropic distillation using a Dean Stark trap. The recovered product weighed 17.3 g and was analyzed by gas chromatography. The product was 75% $(CF_3)_2CHOCH_2F$ and 21% $(CF_3)_2CHOCH_2Cl$. There was 0.5% of $(CF_3)_2CHOH$. Conversion was 83% and yield was 78%.

EXAMPLE 25

A mixture of $(CF_3)_2CHOCH_2Cl$ 21.6 g (0.1 mole), potassium fluoride 8.7 g (0.15 mole), 10 g of water, and 1 g of Aliquat 336 was heated with stirring in a 100 cc autoclave for 16 hours at 60° C. Water was added to dissolve the precipitated salts, and the product was recovered by azeotropic distillation using a Dean Stark trap. The recovered product weighed 17 g and was analyzed by gas chromatography. The product was 68% $(CF_3)_2CHOCH_2F$ and 28% $(CF_3)_2CHOCH_2Cl$. There was 0.5% of $(CF_3)_2CHOH$. Conversion was 78% and yield was 74%.

EXAMPLE 26

A mixture of $(CF_3)_2CHOCH_2Cl$ 21.6 g (0.1 mole), potassium fluoride 8.7 g (0.15 mole), 10 g of water, and 2 g of Aliquat 336 was heated with stirring in a 100 cc autoclave for 16 hours at 60° C. Water was added to dissolve the precipitated salts, and the product was recovered by azeotropic distillation using a Dean Stark trap. The recovered product weighed 17.5 g and was analyzed by gas chromatography. The product was 74.7% $(CF_3)_2CHOCH_2F$ and 17% $(CF_3)_2CHOCH_2Cl$. Conversion was 86% and yield was 76%.

EXAMPLE 27

A mixture of $(CF_3)_2CHOCH_2Cl$ 21.6 g (0.1 mole), potassium fluoride 8.7 g (0.15 mole), 10 g of water, and 1 g of Aliquat 336 was heated with stirring in a 100 cc autoclave for 3 hours at 100° C. Water was added to dissolve the precipitated salts, and the product was recovered by azeotropic distillation using a Dean Stark trap. The recovered product weighed 17.6 g and was analyzed by gas chromatography. The product was 92.2% $(CF_3)_2CHOCH_2F$ and 3.8% $(CF_3)_2CHOCH_2Cl$. Conversion was 97% and yield was 84%.

EXAMPLE 28

A mixture of $(CF_3)_2CHOCH_2Cl$ 21.6 g (0.1 mole), potassium fluoride 6.38 g (0.11 mole), 10 g of water, and 1 g of Aliquat 336 was heated with stirring in a 100 cc autoclave for 3 hours at 100° C. Water was added to dissolve the precipitated salts, and the product was recovered by azeotropic distillation using a Dean Stark trap. The recovered product weighed 17 g and was analyzed by gas chromatography. The product was 84% $(CF_3)_2CHOCH_2F$ and 11% $(CF_3)_2CHOCH_2Cl$. Conversion was 91% and yield was 78%.

EXAMPLE 29

A mixture of $(CF_3)_2CHOCH_2Cl$ 21.6 g (0.1 mole), potassium fluoride 8.7 g (0.15 mole), 10 g of water, and 1 g of Aliquat 100 was heated with stirring in a 100 cc autoclave for 15 hours at 60° C. Water was added to dissolve the precipitated salts, and the product was recovered by azeotropic distillation using a Dean Stark trap. The recovered product weighed 18.3 g and was analyzed by gas chromatography. The product was 77% $(CF_3)_2CHOCH_2F$ and 20% $(CF_3)_2CHOCH_2Cl$. Conversion was 83% and yield was 85%.

EXAMPLE 30

A mixture of $(CF_3)_2CHOCH_2Cl$ 21.6 g (0.1 mole), potassium fluoride 8.7 g (0.15 mole), 10 g of water, and 1 g of Aliquat 100 was heated with stirring in a 100 cc autoclave for 3 hours at 100° C. Water was added to dissolve the precipitated salts, and the product was recovered by azeotropic distillation using a Dean Stark trap. The recovered product weighed 17.7 g and was analyzed by gas chromatography. The product was 87% $(CF_3)_2CHOCH_2F$ and 8% $(CF_3)_2CHOCH_2Cl$. There was 2.6% of $(CF_3)_2CHOH$. Conversion was 93% and yield was 83%.

EXAMPLE 31

A mixture of $(CF_3)_2CHOCH_2Cl$ 21.6 g (0.1 mole), potassium fluoride 8.7 g (0.15 mole), 20 g of water, and 1.7 g of Aliquat 100 was heated with stirring in a 100 cc autoclave for 15 hours at 60° C. Water was added to dissolve the precipitated salts, and the product was recovered by azeotropic distillation using a Dean Stark trap. The recovered product weighed 18.2 g and was analyzed by gas chromatography. The product was 75% $(CF_3)_2CHOCH_2F$ and 23% $(CF_3)_2CHOCH_2Cl$. There was 0.4% of $(CF_3)_2CHOH$. Conversion was 81% and yield was 85%.

EXAMPLE 32

A mixture of $(CF_3)_2CHOCH_2Cl$ 21.6 g (0.1 mole), potassium fluoride 6.38 g (0.11 mole), 10 g of water, and 1 g of Aliquat 336 was heated with stirring in a 100 cc autoclave for 3 hours at 100° C. Water was added to dissolve the precipitated salts, and the product was recovered by azeotropic distillation using a Dean Stark trap. The recovered product weighed 18.1 g and was analyzed by gas chromatography. The product was 81% $(CF_3)_2CHOCH_2F$ and 15% $(CF_3)_2CHOCH_2Cl$. There was 1.5% of $(CF_3)_2CHOH$. Conversion was 87% and yield was 85%.

EXAMPLE 33

A mixture of $(CF_3)_2CHOCH_2Cl$ 21.6 g (0.1 mole), potassium fluoride 6.38 g (0.11 mole), 20 g of water, and 1 g of Aliquat 336 was heated with stirring in a 100 cc autoclave for 5 hours at 100° C. Water was added to dissolve the precipitated salts, and the product was recovered by azeotropic distillation using a Dean Stark trap. The recovered product weighed 16.8 g and was analyzed by gas chromatography. The product was 78% $(CF_3)_2CHOCH_2F$ and 10% $(CF_3)_2CHOCH_2Cl$. There was 9.9% of $(CF_3)_2CHOH$. Conversion was 92% and yield was 71%.

EXAMPLE 34

A mixture of $(CF_3)_2CHOCH_2Cl$ 43.2 g (0.2 mole), potassium fluoride 12.76 g (0.22 mole), 10 g of water, and 2 g of Aliquat 336 was heated with stirring in a 100 cc autoclave for 3 hours at 100° C. Water was added to dissolve the precipitated salts, and the product was recovered by azeotropic distillation using a Dean Stark trap. The recovered product weighed 36.2 g and was analyzed by gas chromatography. The product was 79% $(CF_3)_2CHOCH_2F$ and 15% $(CF_3)_2CHOCH_2Cl$. There was 2.5% of $(CF_3)_2CHOH$. Conversion was 87% and yield was 82%.

EXAMPLE 35

A mixture of $(CF_3)_2CHOCH_2Cl$ 21.6 g (0.1 mole), potassium fluoride 6.38 g (0.11 mole), 10 g of water, and 1 g of Aliquat 336 was heated with stirring in a 100 cc autoclave for 6 hours at 100° C. Water was added to dissolve the precipitated salts, and the product was recovered by azeotropic distillation using a Dean Stark trap. The recovered product weighed 18.6 g and was analyzed by gas chromatography. The product was 78.3% $(CF_3)_2CHOCH_2F$ and 17% $(CF_3)_2CHOCH_2Cl$. There was 1.4% of $(CF_3)_2CHOH$. Conversion was 85% and yield was 86%.

EXAMPLE 36

A mixture of $(CF_3)_2CHOCH_2Cl$ 21.6 g (0.1 mole), potassium fluoride 8.7 g (0.15 mole), 10 g of water, and 1 g of Aliquat 336 was heated with stirring in a 100 cc autoclave for 3 hours at 100° C. Water was added to dissolve the precipitated salts, and the product was recovered by azeotropic distillation using a Dean Stark trap. The recovered product weighed 16.9 g and was analyzed by gas chromatography. The product was 90.3% $(CF_3)_2CHOCH_2F$ and 6.2% $(CF_3)_2CHOCH_2Cl$. There was 0.23% of $(CF_3)_2CHOH$. Conversion was 95% and yield was 80%.

EXAMPLE 37

A mixture of $(CF_3)_2CHOCH_2Cl$ 21.6 g (0.1 mole), potassium fluoride 8.7 g (0.15 mole), 10 g of water, and 0.5 g of Aliquat 336 was heated with stirring in a 100 cc autoclave for 3 hours at 100° C. Water was added to dissolve the precipitated salts, and the product was recovered by azeotropic distillation using a Dean Stark trap. The recovered product weighed 17.5 g and was analyzed by gas chromatography. The product was 80.5% $(CF_3)_2CHOCH_2F$ and 15% $(CF_3)_2CHOCH_2Cl$. There was 0.12% of $(CF_3)_2CHOH$. Conversion was 88% and yield was 80%.

EXAMPLE 38

A mixture of $(CF_3)_2CHOCH_2Cl$ 21.6 g (0.1 mole), potassium fluoride 6.38 g (0.11 mole), 10 g of water, and 1 g of Aliquat 336 was heated with stirring in a 100 cc autoclave for 3 hours at 120° C. Water was added to dissolve the precipitated salts, and the product was recovered by azeotropic distillation using a Dean Stark trap. The recovered product weighed 16.8 g and was analyzed by gas chromatography. The product was 88.6% $(CF_3)_2CHOCH_2F$ and 6.8% $(CF_3)_2CHOCH_2Cl$. There was 2.1% of $(CF_3)_2CHOH$. Conversion was 95% and yield was 79%.

EXAMPLE 39

A mixture of $(CF_3)_2CHOCH_2Cl$ 43.2 g (0.2 mole), potassium fluoride 12.8 g (0.22 mole), 7.92 g of water, and 1 g of tetraethyl ammonium chloride was heated with stirring in a 100 cc autoclave for 3 hours at 100° C. Water was added to dissolve the precipitated salts, and the product was recovered by azeotropic distillation using a Dean Stark trap. The recovered product weighed 37 g and was analyzed by gas chromatography. The product was 79% $(CF_3)_2CHOCH_2F$ and 17% $(CF_3)_2CHOCH_2Cl$. Conversion was 85% and yield was 86%.

EXAMPLE 40

A mixture of 43.2 g of $(CF_3)_2CHOCH_2Cl$ (0.2 mole), 20.7 g of potassium fluoride dihydrate (0.22 mole), and 1 g of Aliquat HTA-1 was heated with stirring in a 100 cc autoclave for 3 hours at 100° C. The product was recovered by azeotropic distillation from water using a Dean Stark trap. The recovered product weighed 37 g and was analyzed by gas chromatography. The product was 67% of $(CF_3)_2CHOCH_2F$ and 31% $(CF_3)_2CHOCH_2Cl$. Conversion was 73% and yield was 85%.

EXAMPLE 41

A mixture of 43.2 g of $(CF_3)_2CHOCH_2Cl$ (0.2 mole), 18.8 g of potassium fluoride dihydrate (0.2 mole), and 1 g of Aliquat HTA-1 was heated with stirring in a 100 cc autoclave for 3 hours at 100° C. The product was recovered by azeotropic distillation from water using a Dean Stark trap. The recovered product weighed 38 g and was analyzed by gas chromatography. The product was 69% of $(CF_3)_2CHOCH_2F$ and 29% $(CF_3)_2CHOCH_2Cl$. Conversion was 74% and yield was 88%.

EXAMPLE 42

A mixture of 43.2 g of $(CF_3)_2CHOCH_2Cl$ (0.2 mole), 18.8 g of potassium fluoride dihydrate (0.2 mole), 1.56 g (0.02 mole) of $KHF_2$, and 1 g of Aliquat HTA-1 was heated with stirring in a 100 cc autoclave for 13 hours at 100° C. The product was recovered by azeotropic distillation from water using a Dean Stark trap. The recovered product weighed 37.8 g and was analyzed by gas chromatography. The product was 79.4% of $(CF_3)_2CHOCH_2F$ and 17.8% $(CF_3)_2CHOCH_2Cl$. There was 1.6% of $(CF_3)_2CHOH$ present. Conversion was 84% and yield was 89%.

EXAMPLE 43

A mixture of 43.2 g of $(CF_3)_2CHOCH_2Cl$ (0.2 mole), 20.7 g of potassium fluoride dihydrate (0.22 mole), and 1 g of tetraethyl ammonium chloride was heated with stirring in a 100 cc autoclave for 3 hours at 100° C. The product was recovered by azeotropic distillation from water using a Dean Stark trap. The recovered product weighed 37 g and was analyzed by gas chromatography. The product was 79% of $(CF_3)_2CHOCH_2F$ and 17% $(CF_3)_2CHOCH_2Cl$. There was 0.08% of $(CF_3)_2CHOH$ present. Conversion was 85% and yield was 86%.

EXAMPLE 44

A mixture of 43.2 g of $(CF_3)_2CHOCH_2Cl$ (0.2 mole), 18.8 g of potassium fluoride dihydrate (0.2 mole), 1.56 g (0.02 mole) of $KHF_2$, and 1 g of Aliquat HTA-1 was heated with stirring in a 100 cc autoclave for 6 hours at 100° C. The product was recovered by washing with water. The recovered product weighed 35.8 g and was analyzed by gas chromatography. The product was 89% of $(CF_3)_2CHOCH_2F$ and 8% $(CF_3)_2CHOCH_2Cl$. There was 2.2% of $(CF_3)_2CHOH$ present. Conversion was 93% and yield was 86%.

EXAMPLE 45

A mixture of 43.2 g of $(CF_3)_2CHOCH_2Cl$ (0.2 mole), 18.8 g of potassium fluoride dihydrate (0.2 mole), and 1 g of Aliquat HTA-1 was heated with stirring in a 100 cc autoclave for 6 hours at 100° C. The product was recovered by azeotropic distillation from water using a Dean Stark trap. The recovered product weighed 37.6 g and was analyzed by gas chromatography. The product was 73% of $(CF_3)_2CHOCH_2F$ and 20% $(CF_3)_2CHOCH_2Cl$. There was 4% of $(CF_3)_2CHOH$ present. Conversion was 83% and yield was 83%.

EXAMPLE 46

A mixture of 43.2 g of $(CF_3)_2CHOCH_2Cl$ (0.2 mole), 20.7 g of potassium fluoride dihydrate (0.22 mole), and 1 g of Aliquat HTA-1 was heated with stirring in a 100 cc autoclave for 3 hours at 100° C. The product was recovered by azeotropic distillation from water using a Dean Stark trap. The recovered product weighed 37.3 g and was analyzed by gas chromatography. The product was 77% of $(CF_3)_2CHOCH_2F$ and 18% $(CF_3)_2CHOCH_2Cl$. There was 3% of $(CF_3)_2CHOH$ present. Conversion was 84% and yield was 85%.

What is claimed is:

1. A process for the preparation of $(CF_3)_2CHOCH_2F$ (sevoflurane), said process comprising forming a reaction mixture of $(CF_3)_2CHOCH_2Cl$, potassium fluoride, water and a phase transfer catalyst, and without the presence of an organic co-solvent, wherein the phase transfer catalyst is selected from the group consisting of: quaternary ammonium salts, quaternary phosphonium salts, and crown ethers, such that sevoflurane is formed.

2. A process as in claim 1, wherein less than 5 wt % of the $(CF_3)_2CHOCH_2Cl$ charged to the reaction vessel is hydrolyzed.

3. A process as in claim 1, wherein greater than 50% of the molar amount of $(CF_3)_2CHOCH_2Cl$ consumed in the reaction is converted to sevoflurane.

4. A process as in claim 1, wherein the reaction mixture is heated to a temperature in the range of 60 ° C. to 100 ° C., the pressure is in the range of from about 0 psig to 105 psig, and the time is in the range of about 3 to 16 hours.

5. A process as in claim 1, wherein the mixture further comprises hydrochloric acid, hydrofluoric acid, or another inorganic or organic acid at an amount in the range of 1 to 3% based upon the weight of $(CF_3)_2CHOCH_2Cl$ charged to the reaction vessel.

6. A process as in claim 1, wherein the reaction mixture further comprises potassium bifluoride ($KHF_2$) or a potassium fluoride hydrate salt.

7. A process for the preparation of sevoflurane comprising combining, in a reaction vessel, components comprising $(CF_3)_2CHOCH_2Cl$, potassium fluoride, water, and a phase transfer catalyst, and without the presence of an organic co-solvent, wherein the phase transfer catalyst is selected from the group consisting of: quaternary ammonium salts, quaternary phosphonium salts, and crown ethers, to form a reaction mixture wherein the molar amount of potassium fluoride per mole of $(CF_3)_2CHOCH_2Cl$ added is greater than 0.1:1, the phase transfer catalyst is present in amounts greater than 0.25% based upon the weight of the $(CF_3)_2CHOCH_2Cl$ charged to the reaction vessel, and the water is present in amounts such that the weight of potassium fluoride to the combined weight of potassium fluoride and water is greater than 25%; wherein sevoflurane is formed.

8. A process as in claim 7, further comprising heating the reaction mixture to a temperature in the range of 60 ° C. to 100 ° C., wherein the pressure of the reaction is in the range of from about 0 psig to 105 psig.

9. A process as in claim 7 further comprising the step of separating sevoflurane out of the reaction mixture.

10. A process as in claim 8 further comprising the step of separating sevoflurane out of the reaction mixture.

11. A process as in claim 7, wherein the molar amount of potassium fluoride is in the range of from 1:1 to 2:1 moles of potassium fluoride per mole of $(CF_3)_2CHOCH_2Cl$ charged to the reaction vessel, the amount of phase transfer catalyst is in the range of 1 to 5% based upon the weight of $(CF_3)_2CHOCH_2Cl$ charged to the reaction vessel, and the quantity of water is in the range of from 10 to 50% based upon the weight of $(CF_3)_2CHOCH_2Cl$ charged to the reaction vessel.

12. A process as in claim 7, wherein the mixture further comprises hydrochloric acid, hydrofluoric acid, or another inorganic or organic acid at an amount in the range of 1 to 3% based upon the weight of $(CF_3)_2CHOCH_2Cl$ charged to the reaction vessel.

13. A process as in claim 7, wherein the reaction mixture further comprises potassium bifluoride ($KHF_2$) or a potassium fluoride hydrate salt.

14. A process as in claim 7, wherein less than 5 wt % of the $(CF_3)_2CHOCH_2Cl$ charged to the reaction vessel is hydrolyzed and greater than 50% of the molar amount of $(CF_3)_2CHOCH_2Cl$ consumed in the reaction is converted to sevoflurane.

15. A process as in claim 1 further comprising the step of separating the sevoflurane out of the reaction mixture.

16. The process of claim 1 wherein the quaternary ammonium salt is selected from the group consisting of: methyl tetrabutyl ammonium chloride, tricapryl methylammonium chloride, and benzyl triethyl ammonium chloride.

17. The process of claim 1 wherein the quaternary phosphonium salt is selected from the group consisting of: butyl triphenyl phosphonium chloride and methyl triphenyl phosphonium bromide.

18. The process of claim 1 wherein the crown ether is selected from the group consisting of: 18-crown-6 and dibenzo-18-crown-6.

19. The process of claim 7 wherein the quaternary ammonium salt is selected from the group consisting of: methyl tetrabutyl ammonium chloride, tricapryl methylammonium chloride, and benzyl triethyl ammonium chloride.

20. The process of claim 7 wherein the quaternary phosphonium salt is selected from the group consisting of: butyl triphenyl phosphonium chloride and methyl triphenyl phosphonium bromide.

21. The process of claim 7 wherein the crown ether is selected from the group consisting of: 18-crown-6 and dibenzo-18-crown-6.

* * * * *